United States Patent [19]
Eckhardt et al.

[11] Patent Number: 5,733,341
[45] Date of Patent: Mar. 31, 1998

[54] INHIBITION OF DYE MIGRATION IN A WASH LIQUOR

[75] Inventors: Claude Eckhardt, Riedisheim, France; Dieter Reinehr, Kandern, Germany; Georges Metzger, Moernach, France

[73] Assignee: Ciba Specialty Chemicals Corporation, Tarrytown, N.Y.

[21] Appl. No.: 572,417

[22] Filed: Dec. 14, 1995

[30] Foreign Application Priority Data

Dec. 15, 1994 [GB] United Kingdom ............... 9425296

[51] Int. Cl.$^6$ .............. C11D 3/30; C11D 3/395; C11D 7/10; D06L 3/02
[52] U.S. Cl. .......... 8/111; 8/111; 8/137; 510/500; 510/360; 510/475; 510/446; 510/413; 510/414; 510/299; 510/302; 510/303; 510/304; 510/309; 510/499; 556/32; 556/33; 556/45; 546/2; 546/6
[58] Field of Search ................ 556/32, 33, 45; 546/2, 6; 510/500, 360, 475, 446, 413, 414, 299, 302, 303, 304, 309, 499

[56] References Cited

U.S. PATENT DOCUMENTS 5,462,564 10/1995 Eckhardt et al. .................. 8/111

FOREIGN PATENT DOCUMENTS

93/03838 3/1993 WIPO.

OTHER PUBLICATIONS

Chemical Abstract, 117:61600.
Chemical Abstract, 81:72056.
Chemical Abstract, 72:132217.
Chemical Abstract: 123: 116295.
Chemical Abstract: 121: 49055.
Chemical Abstract: 120: 44496.

*Primary Examiner*—Paul Lieberman
*Assistant Examiner*—Charles Boyer
*Attorney, Agent, or Firm*—Kevin T. Mansfield

[57] ABSTRACT

A process is described for inhibiting the re-absorption of migrating dyes in the wash liquor, comprising introducing into a wash liquor containing a peroxide-containing detergent, from 0.5 to 150, preferably from 1.5 to 75, especially from 7.5 to 40 mg. per liter of wash liquor, of one or more compounds having the formula (1), (2), (3), (4), (5), (6), (7), (8), (9), (10), (11), (12), (13) or (14) as defined in the specification. The compounds of formula (1), (2), (3), (4), (5), (6), (8), (9) (10), (11), (12), (13) or (14) are new compounds. The compounds used do not exhaust at all on to cotton, polyamide or polyester fibers, so that the compounds cannot lead to fiber discoloration problems.

27 Claims, No Drawings

INHIBITION OF DYE MIGRATION IN A WASH LIQUOR

The present invention relates to a process for inhibiting the re-absorption of migrating dyes in the wash liquor.

It is well known that various metal compounds, e.g. manganese complexes, are useful in detergents as catalysts for peroxides.

It has now been found that certain other manganese complexes exert a pronounced bleaching effect on dirt or dyes in the wash bath. Moreover, these manganese complexes do not exhaust at all on to cotton, polyamide or polyester fibres so that the complexes cannot lead to fibre discolouration problems.

Accordingly, the present invention provides a process for inhibiting the re-absorption of migrating dyes in the wash liquor, comprising introducing into a wash liquor containing a peroxide-containing detergent, from 0.5 to 150, preferably from 1.5 to 75, especially from 7.5 to 40 mg. per liter of wash liquor, of one or more compounds having the formula (1), (2), (3), (4), (5), (6), (7), (8), (9), (10), (11), (12), (13) or (14):

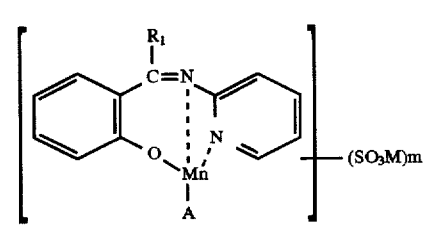  (1)

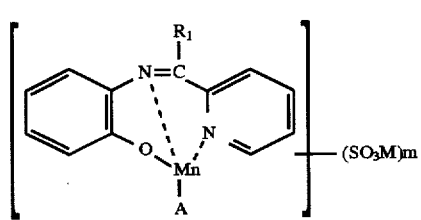  (2)

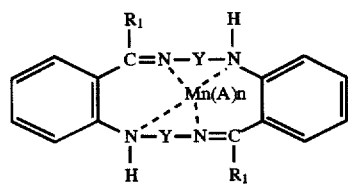  (3)

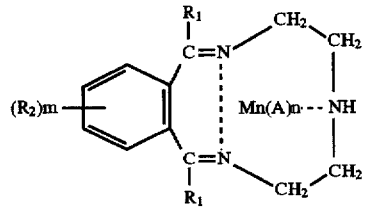  (4)

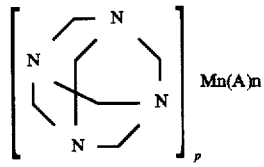  (5)

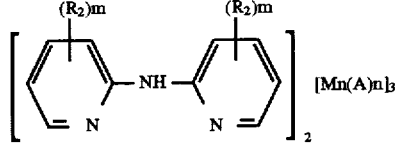  (6)

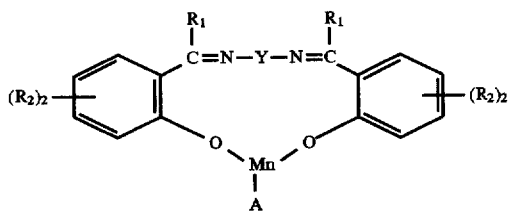  (7)

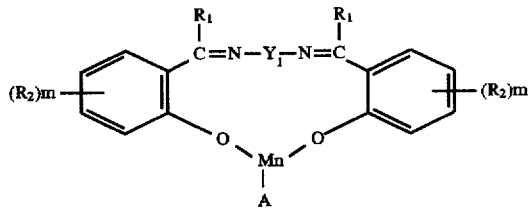  (8)

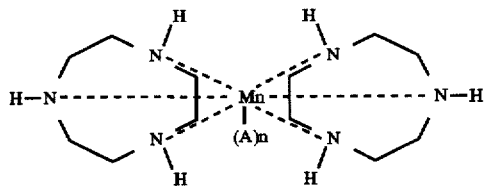  (9)

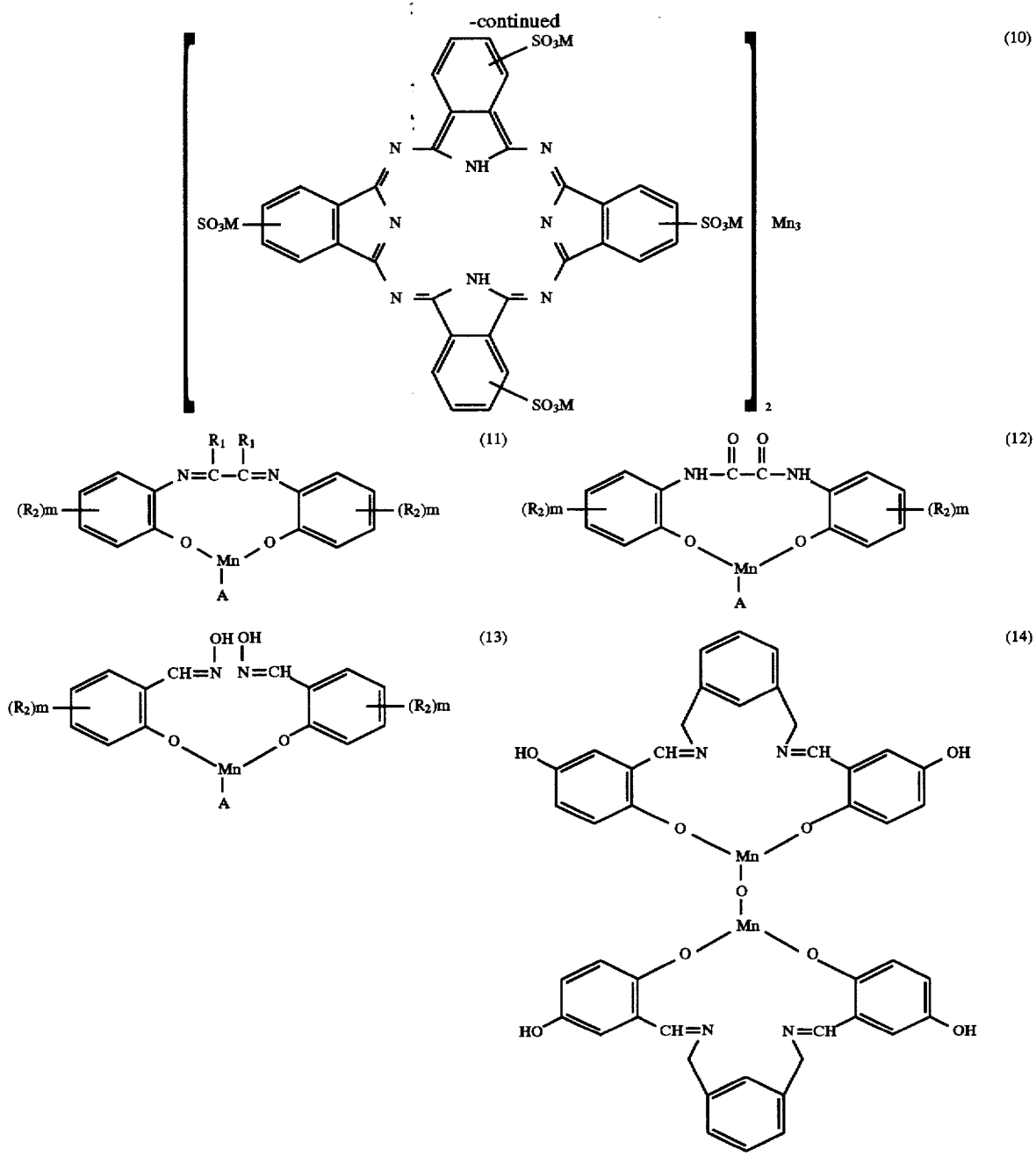

in which $R_1$ is hydrogen or optionally substituted alkyl, cycloalkyl or aryl; $R_2$ is hydrogen, optionally substituted alkyl, optionally substituted alkoxy, halogen, cyano, N(optionally substituted alkyl)$_2$, N$^{\oplus}$(optionally substituted alkyl)$_3$ or a water-solubilising group, especially) SO$_3$M; Y is optionally substituted alkylene, cyclohexylene or arylene; $Y_1$ is $C_2$–$C_4$ alkylene, optionally interrupted by a nitrogen atom, a 1,4-methanocyclohexylene residue or a phenylene residue optionally substituted by a group SO$_3$M; M is hydrogen, an alkali metal atom, ammonium or a cation formed from an amine; n is 2 or 3; m is 0 or 1; p is 1 or 2; and A is an anion.

When one or both of $R_1$ and $R_2$ are or contain optionally substituted alkyl, preferred alkyl groups are $C_1$–$C_8$-, especially $C_1$–$C_4$-alkyl groups. The alkyl groups may be branched or unbranched and may be optionally substituted, e.g. by halogen such as fluorine, chlorine or bromine, by $C_1$–$C_4$-alkoxy such as methoxy or ethoxy, by phenyl or carboxyl, by $C_1$–$C_4$-alkoxycarbonyl such as acetyl, or by a mono- or di-alkylated amino group.

When $R_1$ is cycloalkyl, this may also be substituted, e.g. by $C_1$–$C_4$-alkyl or $C_1$–$C_4$-alkoxy.

When $R_1$ is optionally substituted aryl, it is preferably a phenyl or naphthyl group each of which may be substituted by $C_1$–$C_4$-alkyl, e.g. by methyl, ethyl, propyl, isopropyl, butyl, isobutyl, sec.-butyl or tert.-butyl, by $C_1$–$C_4$-alkoxy such as methoxy, ethoxy, propoxy, isopropoxy, butoxy, isobutoxy, sec.-butoxy or tert.-butoxy, by halogen such as fluorine, chlorine or bromine, by $C_2$–$C_5$-alkanoylamino, such as acetylamino, propionylamino or butyrylamino, by nitro, sulpho or by dialkylated amino.

Optionally substituted alkoxy groups $R_2$ are preferably $C_1$–$C_8$-, especially $C_1$–$C_4$-alkoxy groups. The alkoxy groups may be branched or unbranched and may be optionally substituted, e.g. by halogen such as fluorine, chlorine or bromine, by $C_1$–$C_4$-alkoxy such as methoxy or ethoxy, by phenyl or carboxyl, by $C_1$–$C_4$-alkoxycarbonyl such as acetyl, or by a mono- or di-alkylated amino group.

Halogen atoms $R_2$ are preferably bromo or, especially, chloro atoms.

N(optionally substituted alkyl)$_2$ groups $R_2$ are preferably N(optionally substituted $C_1$–$C_4$alkyl)$_2$ groups, especially N(methyl)$_2$ or N(ethyl)$_2$.

$N^{\oplus}$(optionally substituted alkyl)$_3$ groups $R_2$ are $N^{\oplus}$(optionally substituted $C_1$–$C_4$alkyl)$_3$, especially $N^{\oplus}$(methyl)$_3$ or $N^{\oplus}$(ethyl)$_3$.

When Y is alkylene, it is preferably a $C_2$–$C_4$-alkylene residue, especially a —$CH_2$—$CH_2$— bridge. Y may also be a $C_2$–$C_8$-alkylene residue which is interrupted by oxygen or, especially, by nitrogen, in particular the —$(CH_2)_3$—NH—$(CH_2)_3$— or —$(CH_2)_2$—NH—$(CH_2)_2$ bridge. When Y is a cyclohexylene residue, it may be a monocyclic cyclohexylene ring or a bicyclic cyclohexylene ring, such as a 1,4- methano-cyclohexylene ring. Arylene residues Y include naphthylene and, especially, phenylene residues, bonded in the 1,2-, 1,3- or 1,4-positions.

When Y is optionally substituted arylene, the substituents are preferably $C_1$–$C_4$-alkyl, e.g. methyl, ethyl, propyl, isopropyl, butyl, isobutyl, sec.-butyl or tert-butyl, $C_1$–$C_4$-alkoxy such as methoxy, ethoxy, propoxy, isopropoxy, butoxy, isobutoxy, sec.-butoxy or tert-butoxy, halogen such as fluorine, chlorine or bromine, $C_2$–$C_5$-alkanoylamino, such as acetylamino, propionylamino or butyrylamino, nitro, an $SO_3M$ or $CO_2M$ group, in which M has its previous significance, or di-$C_1$–$C_4$alkylamino.

Anions A include halide, especially chloride, sulphate, nitrate, hydroxy, methoxy, $BF_4$, $PF_6$, carboxylate, especially acetate, triflate or tosylate.

With respect to the compounds of formula (1) or (2), preferably $R_1$ is hydrogen, m is 0 and A is acetate.

In relation to the compounds of formula (3), preferably $R_1$ is hydrogen, m is 0, n is 2 or 3 and A is acetate.

With respect to the compounds of formula (4), preferred compounds are those in which $R_1$ is hydrogen, m is 0, n is 2 and A is $C_1$.

With respect to the compounds of formula (5), preferred compounds are those in which n is 2 and A is chloride.

As to the compounds of formula (6), preferably m is 0, n is 2 and A is acetate.

In relation to the compounds of formula (7), $R_1$ is preferably hydrogen, Y is preferably 1,2-cyclohexylene, $R_2$ is preferably $C_1$–$C_4$alkyl, especially t-butyl and A is preferably acetate.

With respect to the compounds of formula (8), $R_1$ is preferably hydrogen, $Y_1$ is preferably $C_2$–$C_4$ alkylene, optionally interrupted by a nitrogen atom, a 1,4-methanocyclohexylene residue or a phenylene residue substituted by a group $SO_3M$, in which M has its previous significance, $R_2$ is preferably hydrogen or a group $SO_3M$, in which M has its previous significance and A is preferably OH.

In relation to the compounds of formula (9), n is preferably 2 and A is preferably perchlorate.

In relation to compounds of formula (11), $R_1$ is preferably hydrogen, and with respect to compounds of formula (11), (12) and (13), m is preferably 0 and A is preferably OH.

In each of the compounds of formula (1) to (14), it is preferred that they are used in neutral form, i.e. that M, when present, is other than hydrogen, preferably a cation formed from an alkali metal, in particular sodium, or from an amine.

Moreover, in each of the compounds of formula (1) to (14), the respective benzene rings may contain, in addition to any sulpho group, one or more further substituents such as $C_1$–$C_4$-alkyl, $C_1$–$C_4$-alkoxy, halogen, cyano or nitro.

The manganese complexes of formula (1) to (6) and (8) to (14) are believed to be new compounds and, as such, form a further aspect of the present invention. They may be produced by known methods, e.g. by the methods analogous to those disclosed in U.S. Pat. No. 4,655,785 relating to similar copper complexes.

The compounds of formula (7) are described, at least in part, in WO 93/03838.

The present invention also provides a detergent composition comprising:

i) 5–90%,preferably 5–70% of A) an anionic surfactant and/or B) a nonionic surfactant;

ii) 5–70%, preferably 5–50%, especially 5–40% of C) a builder;, iii) 0.1–30%, preferably 1–12% of D) a peroxide; and iv) 0.005–2%, preferably 0.02–1%, especially 0.1–0.5% of E) a compound of formula (1) to (14) as defined above, each by weight, based on the total weight of the detergent.

The detergent may be formulated as a solid; or as a non-aqueous liquid detergent, containing not more than 5, preferably 0–1 wt. % of water, and based on a suspension of a builder in a non-ionic surfactant, as described, e.g., in GB-A-2158454.

Preferably, the detergent is in powder or granulate form.

Such powder or granulate forms may be produced by firs fly forming a base powder by spray-drying an aqueous slurry containing all the said components, apart from the components D) and E); then adding the components D) and E) by dry-blending them into the base powder. In a further process, the component E) may be added to an aqueous slurry containing components A), B) and C), followed by spray-drying the slurry prior to dry-blending component D) into the mixture. In a still further process, component B) is not present, or is only partly present in an aqueous slurry containing components A) and C); component E) is incorporated into component B), which is then added to the spray-dried base powder;, and finally component D) is dry-blended into the mixture.

The anionic surfactant component A) may be, e.g., a sulphate, sulphonate or carboxylate surfactant, or a mixture of these.

Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula R—CO($R^1$)$CH_2COOM^1$ in which R is alkyl or alkenyl having 9–17 carbon atoms in the alkyl or alkenyl radical, $R^1$ is $C_1$–$C_4$ alkyl and $M^1$ is alkali metal.

The nonionic surfactant component B) may be, e.g., a condensate of ethylene oxide with a $C_9$–$C_{15}$ primary alcohol having 3–8 moles of ethylene oxide per mole.

The builder component C) may be an alkali metal phosphate, especially a tripolyphosphate; a carbonate or bicarbonate, especially the sodium salts thereof; a silicate; an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula $NaHSi_mO_{2m+1} \cdot pH_2O$ or $Na_2Si_mO_{2m+1} \cdot pH_2O$ in which m is a number from 1.9 to 4 and p is 0 to 20.

Preferred aluminosilicate are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

The peroxide component D) may be any organic or inorganic peroxide compound, described in the literature or available on the market, which bleaches textiles at conventional washing temperatures, e.g. temperatures in the range of from 10° C. to 90° C. In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides. Peroxides can have different crystalline forms and/or different degrees of hydration. They may be used in admixture with other organic or inorganic salts, thereby improving their stability to storage.

The addition of the peroxides to the detergent is effected, in particular, by mixing the components, for example by means of screw-metering systems and/or fluidized bed mixers.

The detergents may contain, in addition to the combination according to the invention, one or more of fluorescent whitening agents, such as a bis-triazinylamino-stilbene-disulphonic acid, a bis-triazolyl-stilbene-disulphonic acid, a bis-styryl-biphenyl, a bis-benzofuranylbiphenyl, a bis-benzoxalyl derivative, a bis-benzimidazolyl derivative, a coumarine derivative or a pyrazoline derivative; soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; enzymes, such as amylases; photobleaching agents; pigments; and/or shading agents. These constituents should, of course, be stable to the bleaching system employed.

A particularly preferred detergent co-additive is a polymer known to be useful in preventing the transfer of labile dyes between fabrics during the washing cycle. Preferred examples of such polymers are polyvinyl pyrrolidones, optionally modified by the inclusion of an anionic or cationic substituent, especially those having a molecular weight in the range from 5000 to 60,000, in particular from 10,00 to 50,000. Preferably, such polymer is used in an amount ranging from 0.05 to 5%, preferably 0.2–1.7% by weight, based on the weight of the detergent.

The following Examples serve to illustrate the invention; parts and percentages are by weight, unless otherwise stated.

EXAMPLE 1

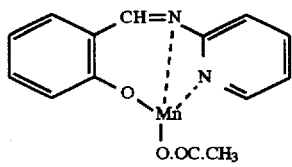

A) To a solution of 18.8 g. of 2-aminopyridine in 300 ml. of ethanol, there are added 24.4 g. of salicylaldehyde. The mixture is heated to 70°–75° C. and stirred for 7 hours. The mixture is concentrated to one third of its volume and then cooled to 5° C., whereupon an orange product having the formula:

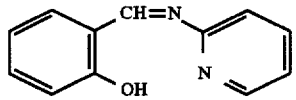

crystallised out. The product is filtered off with suction and allowed to dry in the air, giving a yield of 25.5 g. (65% of theory).

Elemental analysis of the compound having the formula (101a) and having the empirical formula $C_{12}H_{10}N_2O$ gives:

Req. % C 72.71; H 5.08; N 14.13. Found % C 72.6; H 5.1; N 14.1.

B) To a solution of 5.9 g. of the compound of formula (101a) obtained in Part A), in 200 ml. of ethanol, there are added 8.5 g. of manganese-III-acetate dihydrate. The resulting dark brown solution is stirred for 5 hours at 60°–65° C. and evaporated to dryness. The residue is dried in vacuum giving a yield of 6.3 g. (68% of theory) of a light brown compound having the formula (101).

Elemental analysis of the compound having the formula (101) and having the empirical formula $C_{14}H_{12}MnN_2O_3 \cdot CH_3COOH$ gives:

Req. % C 49.48; H 4.38; N 7.22; Mn 14.17. Found % C 50.18; H 4.45; N 7.40; Mn 14.4.

EXAMPLE 2

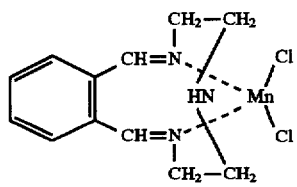

A) To a solution of 26.8 g. phthaldialdehyde in 1000 ml. of ethanol them are added 21.5 ml. of diethylenetriamine and the mixture is stirred for 20 hours at 25° C. The resulting solution becomes brown-green in colour and is evaporated to dryness giving 40 g. (100% theory) of a thick brown liquid having the formula:

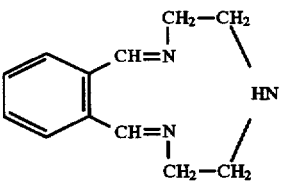

B) To a solution of 19.8 g. of manganese-II-chloride tetrahydrate in 250 ml. of ethanol, there is added a solution of 20.1 g. of the product of formula (102a) in 250 ml. of ethanol. An ochre yellow suspension is formed and this is stirred for 18 hours at 25° C. The product is filtered off with suction, washed with ethanol and dried in vacuum at 25° C. giving 28 g. (85% theory) of an ochre yellow of formula (102).

Elemental analysis of the compound having the formula (102) and having the empirical formula $C_{12}H_{14}Cl_2MnN_3$ gives:

Req. % C 37.81; H 5.55; N 11.02; $C_{1\ 18.60}$; Mn 14.41. Found % C 38.0; H 5.0; N 10.5; Cl 19; Mn 15.4.

EXAMPLE 3

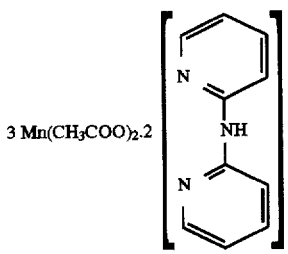
(103)

3 Mn(CH₃COO)₂.2

To a solution of 5.1 g. of 2,2'-dipyridylamine in 50 ml. of ethanol them are added 7.4 g. of manganese-II-acetate tetrahydrate and the mixture is stirred for 18 hours at 25° C. The product is filtered off with suction, washed with methanol and dried in vacuum at 25° C. giving 6.6 g. (58% theory) of a whim product having the formula (103).

Elemental analysis of the compound having the formula (103) and having the empirical formula $C_{32}H_{36}Mn_3N_6O_{12}$ gives:

Req. % C 44.62; H 4.21; N 9.16; Mn 19.13. Found % C 44.70; H 4.15; N 9.12; Mn 19.8.

EXAMPLE 4

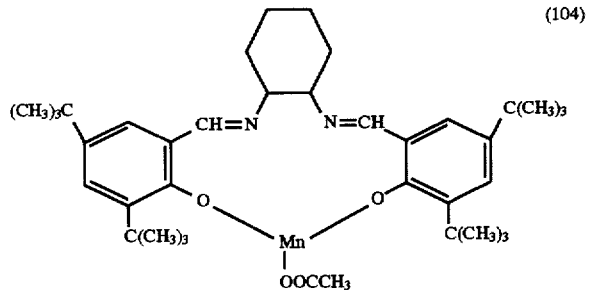
(104)

8.2 g. of 1,2-bis(3,5-di-tert. butylsalicylidamino) cyclohexane are added to 400 ml. of ethanol, the mixture is heated to 65° C. and 3.7 g. of manganese-II-acetate tetrahydrate are added to the yellow suspension. After a short time, a dark brown solution is formed which is stirred for 15 hours and then evaporated to dryness. 9.5 g. (92.8% theory) of a dark brown powder having the formula (104) are obtained.

Elemental analysis of the compound having the formula (104) and having the empirical formula $C_{38}H_{55}MnN_2O_4$. 1.33 H₂O gives:

Req. % C 66.85; H 8.43; N 4.10; Mn 8.05. Found % C 66.98; H 8.53; N 4.00; Mn 7.82.

EXAMPLE 5

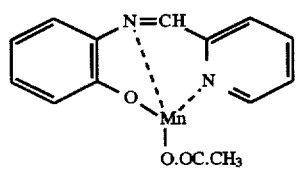
(105)

10.9 g. of o-aminophenol and 10.7 g. of pyridine-2-aldehyde are stirred in 200 ml. of ethanol for 5 hours at 60°–65° C. The solution is then treated with 24.5 g. of manganese-II-acetate tetrahydrate and stirred for 5 hours at 60°–65° C. The solution is evaporated and the residue is dried in vacuum giving 31 g. (95% theory) of a red-brown product having the formula (105).

Elemental analysis of the compound having the formula (105) and having the empirical formula $C_{14}H_{12}MnN_2O_3$. 0.83 H₂O gives:

Req. % C 51.58; H 4.22; N 8.59; Mn 16.87. Found % $C_{51.76}$;N8.11;Mn16.80.

EXAMPLE 6

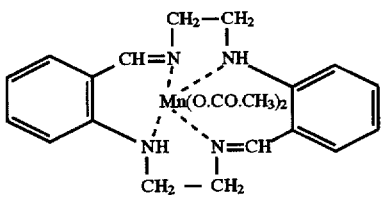
(106)

A) To a solution of 405 ml. of diaminoethane in 1000 ml. of toluene there are added 20 ml. of formic acid and 63.4 g. of copper dust. The suspension is heated to 100° C. and is treated, dropwise, over 2 hours, with a solution of 111 ml. of o-chlorobenzaldehyde in 115 ml. of toluene. After 4 hours at 100° C., the mixture is cooled to 75° C. and some copper dust is filtered off.

The filtrate forms two phases. The upper toluene phase is separated and concentrated to 100 ml. This concentrate is diluted with 200 ml. of ethanol and allowed to stand for 48 hours at 25° C. The product which crystallises out is filtered with suction and dried in vacuum at 40° C. giving 24 g. (16% theory) of a yellow product having the formula:

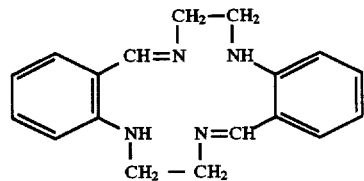
(106a)

B) 5.8 g. of the compound of formula (106a) obtained in Part A) and 5 g. of manganese-II-acetate tetrahydrate are stirred for 12 hours in 200 ml. of ethanol, filtered with suction, washed with ethanol and dried in vacuum, giving 7.5 g. of the compound of formula (106).

Elemental analysis of the compound having the formula (106) and having the empirical formula $C_{22}H_{26}MnN_4O_5$. 0.14 MnO₂ gives:

Req. % C 55.30; H 5.48; N 11.72; Mn 13.12. Found % C 55.34; H 5.55; N 11.80; Mn 12.70.

EXAMPLE 7

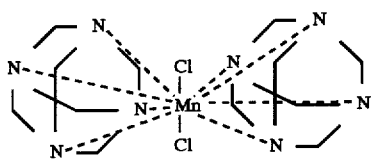
(107)

To a solution of 19.8 g. of manganese-II-chloride in 200 ml. of methanol there are added 14 g. of hexamethylenetetramine. After stirring at 25° C. for 20 hours, the precipitated product is filtered with suction and dried in vacuum at 25° C., giving 18.5 g. (91% theory) of a light grey product having the formula (107).

Elemental analysis of the compound having the formula (107) and having the empirical formula $C_{12}H_{24}Cl_2MnN_8$ 2 $H_2O$ gives:

Req. % C 32.59; H 6.38; N 25.34; Cl 16.03; Mn 12.42. Found % C 32.2; H 6.5; N 24.8; $C1_{16.2}$; Mn 12.4.

EXAMPLE 8

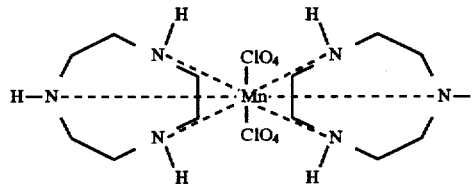
(108)

To a solution of 3 g. of triazacyclononane in 80 ml. of methanol there are added 2 g. of manganese perchlorate hexahydrate. A white suspension is formed immediately. After 30 minutes, 1 g. of sodium acetate is added and the mixture is stirred for 24 hours at 25° C. The product is filtered with suction, washed with methanol and dried in vacuum at 25° C., giving 1.8 g. (65% theory) of a white product having the formula (108).

Elemental analysis of the compound having the formula (108) and having the empirical formula $C_{12}H_{30}Cl_2MnN_6O_8$ gives:

Req. % C 28.12; H 5.86; N 16.41; Cl 13.87; Mn 10.74. Found % C 28.1; H 6.2; N 16.3; $Cl_{13.6}$; Mn 11.0.

EXAMPLE 9

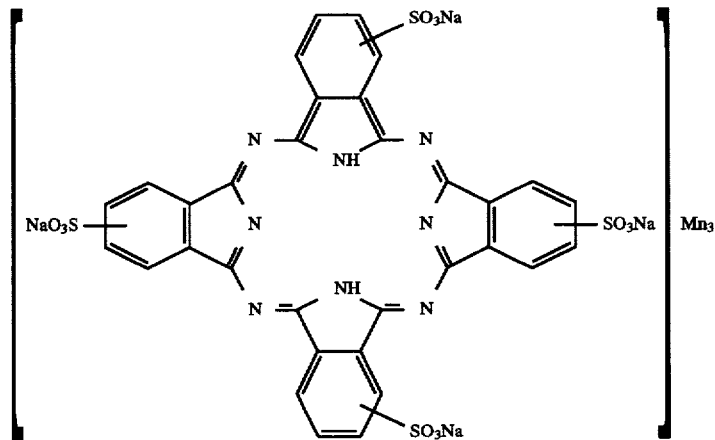

To a solution of 13.8 g. of phthalocyanine tetrasulphonic acid in 140 ml. of water them are added 4.2 g. of manganese-III-acetate dihydrate. The mixture is heated to 70°–75° C. and stirred for 12 hours. 20 g. of sodium chloride are added, the mixture is stirred for a further 6 hours, cooled to 5° C. and filtered with suction. The material filtered off is dissolved in 200 ml. of water and dialysed for 40 hours. The solution remaining is evaporated to dryness and the residue is dried in vacuum, giving 3.5 g. (20% theory) of a black product having the formula (109).

Elemental analysis of the compound having the formula (109) and having the empirical formula $C_{64}H_{40}Mn_3N_{16}O_{24}S_8.22\ H_{20}$ gives:

Req. % C 31.78; H 3.50; N 9.27; S 10.61; Mn 6.81. Found % C 32.1; H 3.2; N 9.4; S 10.7; Mn 6.79.

EXAMPLE 10

Using a procedure similar to that described in Example 4, the compound having the formula (110) is obtained:

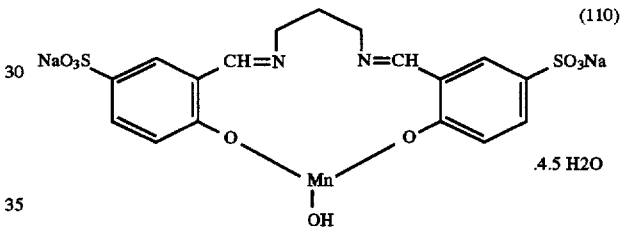
(110)

.4.5 H2O

Elemental analysis of the compound having the formula (110) and having the empirical formula $C_{17}H_{15}MnN_2Na_2O_9S_2.4.5\ H_2O$ gives:

Req. % C 32.57; H 3.77; N 4.44; S 10.22; Mn 8.7. Found % C 32.51; H 3.75; N 4.38; S 9.97; Mn 7.6.

EXAMPLE 11

Using a procedure similar to that described in Example 4, the compound having the formula (111) is obtained:

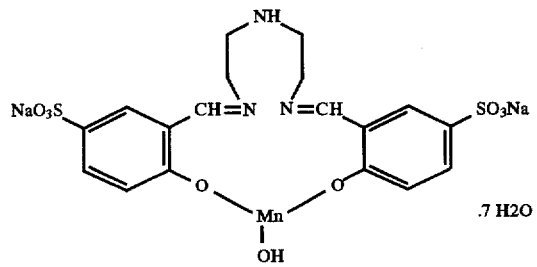
(111)

Elemental analysis of the compound having the formula (111) and having the empirical formula $C_{18}H_{18}MnN_3Na_2O_9S_2 \cdot 0.7\ H_2O$ gives:

Req. % C 30.39; H 4.93; N 5.91; S 9.01; Mn 7.72. Found % C 30.50; H 4.39; N 5.96; S 8.98; Mn 7.36.

EXAMPLE 12

Using a procedure similar to that described in Example 4, the compound having the formula (112) is obtained:

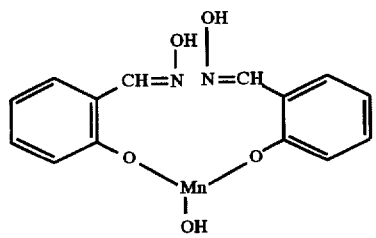
(112)

Elemental analysis of the compound having the formula (112) and having the empirical formula $C_{14}H_{13}MnN_2O_5$ gives:

Req. % C 48.85; H 3.81; N 8.13; Mn 15.96. Found % C 48.44; H 3.82; N 8.07; Mn 16.20.

EXAMPLE 13

Using a procedure similar to that described in Example 4, the compound having the formula (113) is obtained:

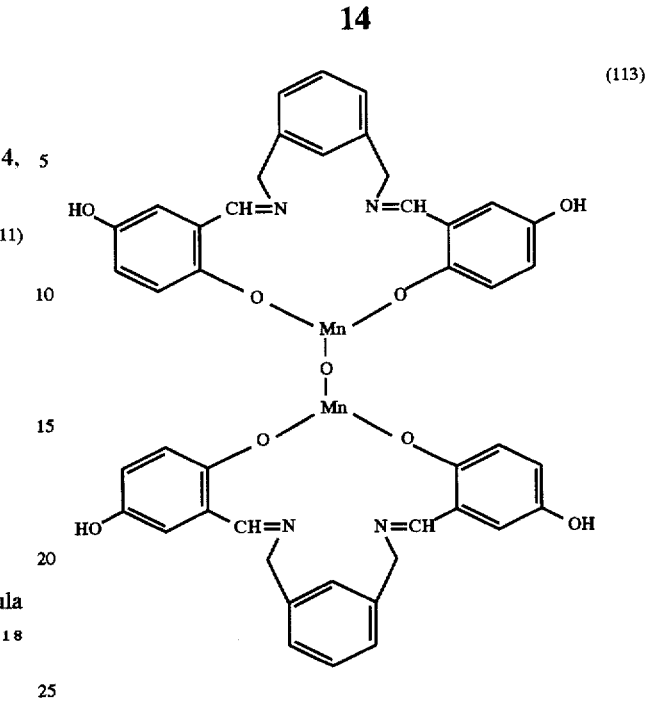
(113)

Elemental analysis of the compound having the formula (113) and having the empirical formula $C_{44}H_{36}Mn_2N_2O_{10} \cdot 0.8\ H_2O$ gives:

Req. % C 51.07; H 5.06; N 5.41; Mn 10.61; O 27.83. Found % C 51.18; H 4.35; N 5.48; Mn 10.3; O 28.69.

EXAMPLE 14

Using a procedure similar to that described in Example 4, the compound having the formula (114) is obtained:

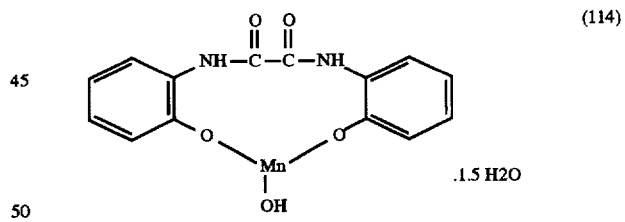
(114)

Elemental analysis of the compound having the formula (114) and having the empirical formula $C_{14}H_{11}MnN_2O_5 \cdot 1.5\ H_2O$ gives:

Req. % C 45.54; H 3.82; N 7.58; Mn 14.80. Found % C 45.57; H 4.04; N 7.63; Mn 13.70.

EXAMPLE 15

Using a procedure similar to that described in Example 4, the compound having the formula (115) is obtained:

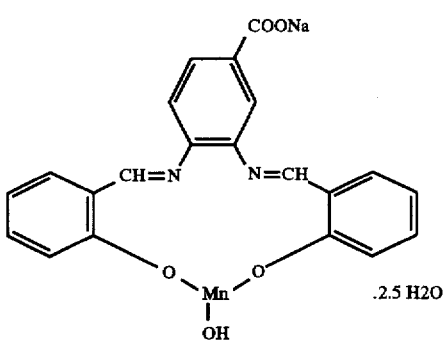

(115)

Elemental analysis of the compound having the formula (115) and having the empirical formula $C_{21}H_{14}MnN_2NaO_5 \cdot 2.5\ H_2O$ gives:

Req. % C 50.72; H 3.85; N 5.63; Mn 12.04; O 24.1. Found % C 50.74; H 3.54; N 5.67; Mn 12.9; O 24.2.

EXAMPLES 16 to 18

The re-uptake of dyes, which have become detached from a coloured article during the washing process and m-absorbed on to goods which are also being washed and which are thereby discoloured, is evaluated using a test dye, as follows:

The following commercial brown dyestuff is tested at a concentration of 10 mg per liter of wash liquor:

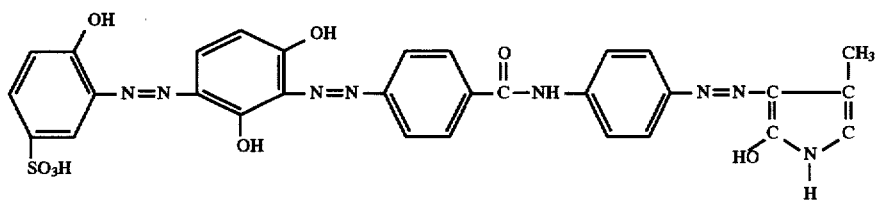

There is then added to this wash liquor, with stirring, in a concentration of 7.5 g. per liter of tap water, a detergent having the following composition:

6% Sodium alkylbenzenesulfonate (®Marion A375);
5% Ethoxylated $C_{14}$–$C_{15}$ fatty alcohol (7 moles EO);
3% Sodium soap;
30 % Zeolite A;
7.5 % Sodium carbonate;
5% Sodium metasilicate ($5.H_2O$);
43.5 % Sodium sulphate.

The pH of the wash liquor is adjusted to pH 11 by the addition of the necessary mount of 0.1N aqueous NaOH solution.

The bath is then tested in a "®Linitest" beaker for 20 minutes at 30°. After the addition, with stirring, directly before the treatment, of x % (see Table 1 below) of sodira perborate monohydrate, and/or of y % (see Table 1 below) of a compound of formula (101), (102) or (103), each based on the weight of the above detergent, a bleached cotton fabric, in an mount of 50g. per liter of wash bath, is also added.

After the wash treatment, over 20 minutes at 30° C., the fabric pieces are rinsed, dried and quickly ironed and their brightness Y is determined using an ICS SF 500 Spectrophotometer.

The difference between the fabric washed without the addition of a dye, and the fabric washed with the addition of the brown dye, viz. "ΔY without bleach system" serves as a control rating for the discolouration.

The effectivity of a bleaching system is determined from the equation:

$$\text{Effectivity in \%} = \frac{\Delta Y \text{ without bleach} - \Delta Y \text{ with bleach}}{\Delta Y \text{ without bleach}} \times 100$$

The results obtained are set out in Table 1:

TABLE 1

| Example | Perborate x % | Compound (101) y % | Effectivity |
|---|---|---|---|
| Control | 0 | 0 | 0% |
| Control | 2 | 0 | 8% |
| 16 | 2 | 0.2 | 69% |

Similar results are obtained when the compound of formula (101) is replaced by a compound having one of the formulae (102; Effectivity 72%; Example 17) or (103; Effectivity 70%; Example 18).

We claim:

1. A process for inhibiting the re-absorption of migrating dyes in a wash liquor, comprising introducing into a wash liquor containing a peroxide-containing detergent, from 0.5 to 150 mg. per liter of wash liquor, of one or more compounds having the formula (1), (2), (3), (4), (5), (6), (9), (10), (11), (12), (13) or (14):

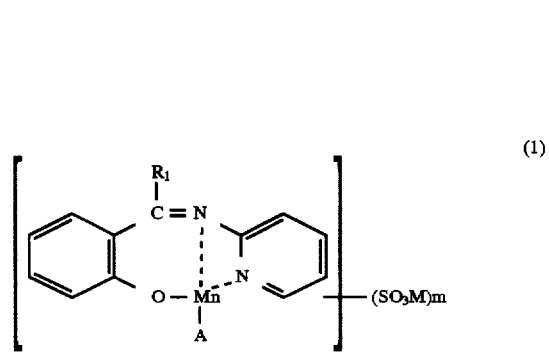

(1)

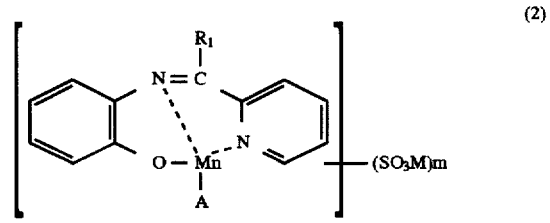

(2)

-continued

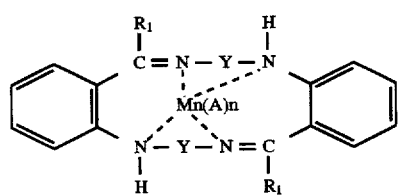
(3)

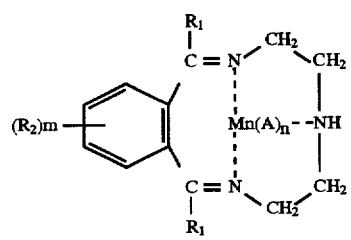
(4)

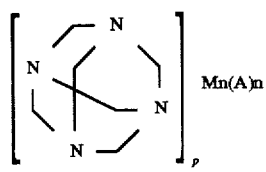
(5)

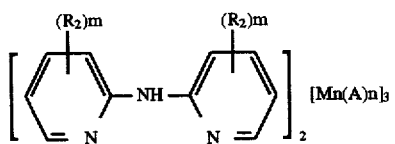
(6)

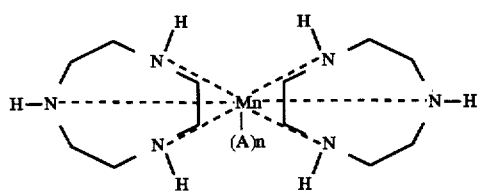
(9)

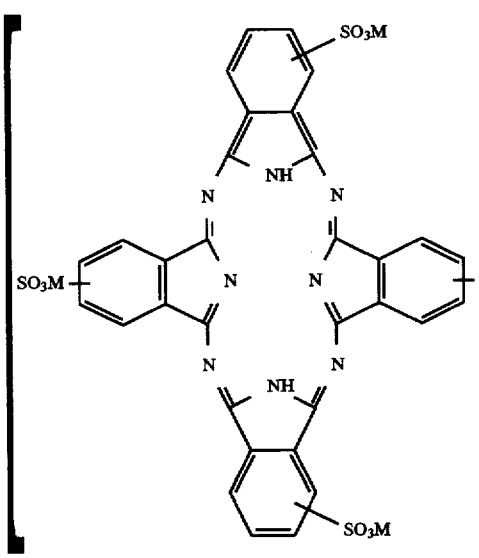
(10)

-continued

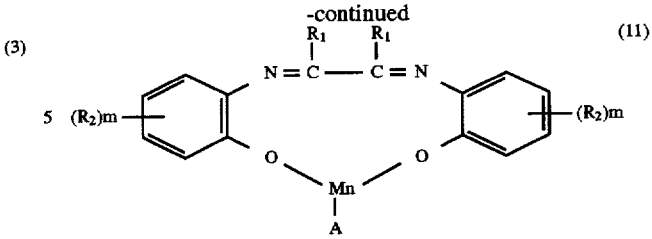
(11)

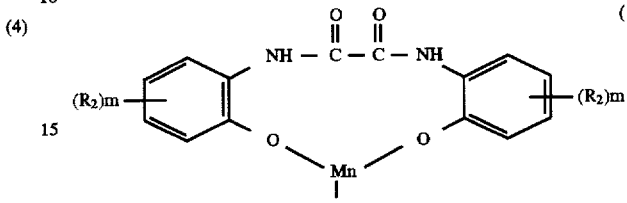
(12)

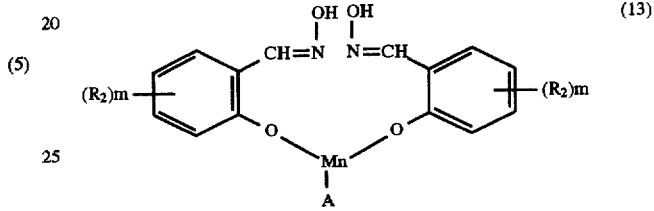
(13)

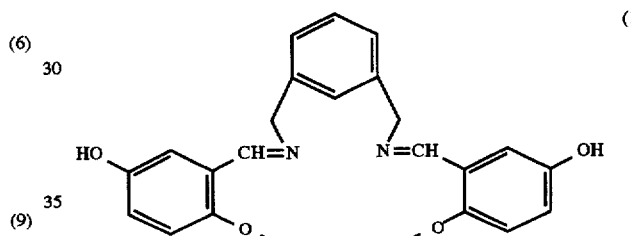
(14)

in which $R_1$ is hydrogen or optionally substituted alkyl, cycloalkyl or aryl;

$R_2$ is hydrogen, optionally substituted alkyl, optionally substituted alkoxy, halogen, cyano, N(optionally substituted alkyl)$_2$, N$^\oplus$(optionally substituted alkyl)$_3$ or a water-solubilising group;

Y is optionally substituted alkylene, cyclohexylene or arylene;

$Y_1$ is $C_2$–$C_4$ alkylene, optionally interrupted by a nitrogen atom, a 1,4-methanocyclohexylene residue, or a phenylene residue optionally substituted by a group SO3M;

M is hydrogen, an alkali metal atom, ammonium or a cation formed from an amine;

n is 2 or 3;

m is 0 or 1;

p is 1 or 2; and

A is an anion.

2. A process according to claim 1 in which from 1.5 to 75 mg. per liter of wash liquor of one or more compounds having the formula (1), (2), (3), (4), (5), (6), (9), (10), (11), (12), (13) or (14) is introduced into the wash liquor.

3. A process according to claim 2 in which from 7.5 to 40 mg. per liter of wash liquor of one or more compounds having the formula (1), (2), (3), (4), (5), (6), (9), (10), (11), (12), (13) or (14) is introduced into the wash liquor.

4. A process according to claim 1 in which the water-solubilising group $R_2$ is $SO_3M$ in which M is as defined in claim 1.

5. A process according to claim 1 in which a compound of formula (1) or (2) is used in which $R_1$ is hydrogen, m is 0 and A is acetate.

6. A process according to claim 1 in which a compound of formula (3) is used in which $R_1$ is hydrogen, m is 0, n is 2 or 3 and A is acetate.

7. A process according to claim 1 in which a compound of formula (4) is used in which $R_1$ is hydrogen, m is 0, n is 2 and A is chloride.

8. A process according to claim 1 in which a compound of formula (5) is used in which n is 2 and A is chloride.

9. A process according to claim 1 in which a compound of formula (6) is used in which m is 0, n is 2 and A is acetate.

10. A process according to claim 1 in which a compound of formula (9) is used in which n is 2 and A is perchlorate.

11. A process according to claim 1 in which a compound of formula (11) is used in which $R_1$ is hydrogen, m is 0 and A is OH.

12. A process according to claim 1 in which a compound of formula (12) or (13) is used in which m is 0 and A is OH.

13. A detergent composition comprising:

i) 5–90% of A) an anionic surfactant and/or B) a nonionic surfactant;

ii) 5–70% of C) a builder;

iii) 0. 1–30% of D) a peroxide; and iv) 0.005–2% or E) a compound of formula (1) to (6) and (9) to (14) as defined in claim 1, each by weight, based on the total weight of the detergent.

14. A composition according to claim 13 comprising:

i) 5–70% of A) an anionic surfactant and/or B) a nonionic surfactant;

ii) 5–50% of C) a builder;.

iii) 1–12% of D) a peroxide; and iv) 0.02–1% of E) a compound of formula (1) to (6) and (9) to (14) as defined in claim 1, each by weight, based on the total weight of the detergent.

15. A composition according to claim 14 comprising:

i) 5–70% of A) an anionic surfactant and/or B) a nonionic surfactant;

ii) 5–40% of C) a builder;

iii) 1–12% of D) a peroxide; and iv) 0.1–0.5% or E) a compound of formula (1) to (6) and (9) to (14) as defined in claim 1, each by weight, based on the total weight of the detergent.

16. A composition according to claim 13 comprising a combination of two or more of the compounds of formula (1) to (6) and (9) to (14).

17. A composition according to claim 13 comprising 0.5–5% by weight of a polymer useful in preventing the transfer of labile dyes between fabrics during a washing cycle.

18. A composition according to claim 17 comprising 0.2–1.7% of the polymer.

19. A composition according to claim 17 in which the polymer is a polyvinylpyrrolidone optionally containing an anionic or cationic substituent.

20. A composition according to claim 13 in which the detergent is in powder or granulate form.

21. A composition according to claim 13 in which the detergent is in liquid form and contains 0–5% water.

22. A composition according to claim 21 in which the detergent is in liquid form and contains 0–1% water.

23. A process for the production of a detergent as claimed in claim 20 in which the components of the detergent are mixed in dry form.

24. A process for the production of a detergent as claimed in claim 20 in which a base powder is produced by spray drying an aqueous slurry which contains all the components defined in claim 15, apart from the components D) and E); and then adding the components D) and E) by dry-blending them into the base powder.

25. A process for the production of a detergent as claimed in claim 20 in which the component E) is added to the slurry containing components A), B) and C), which slurry is then spray-dried before component D) is dry-blended into the mixture.

26. A process for the production, of a detergent as claimed in claim 20 in which component B) is not present, or is only partly present in a slurry containing components A) and C); the component E) is incorporated into component B), which is then added to the spray-dried base powder;and finally component D) is dry-blended into the mixture.

27. A compound having the formula (1), (2), (3), (4), (5), (6), (9), (10), (11), (12), (13) or (14):

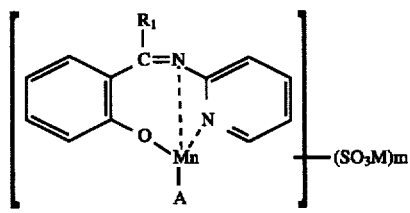
(1)

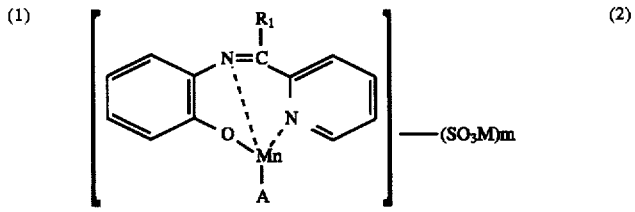
(2)

-continued
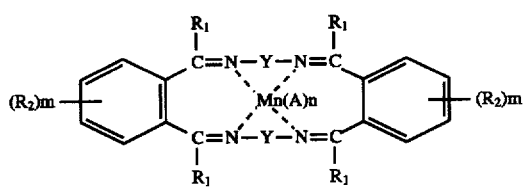 (3)
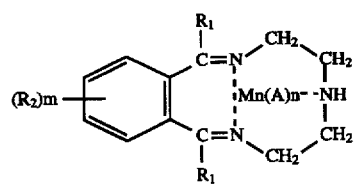 (4)
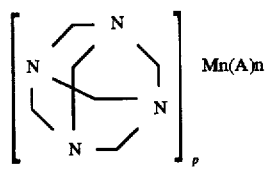 (5)
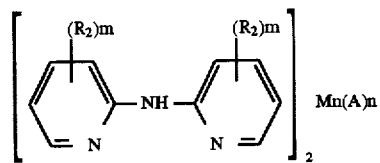 (6)
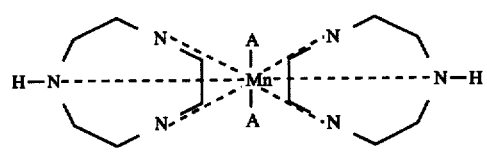 (9)
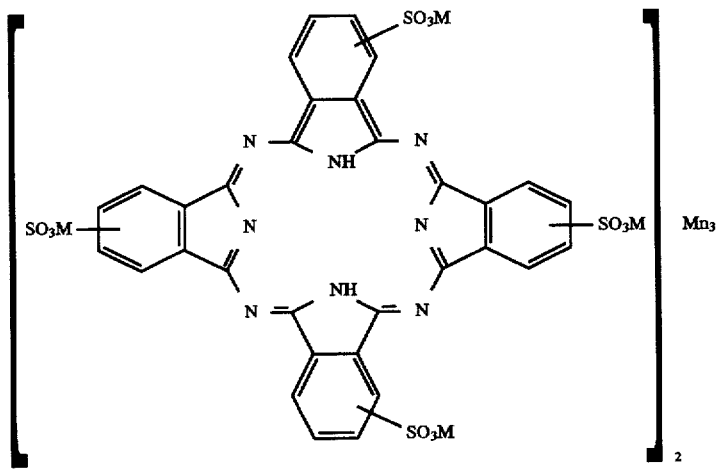 (10)
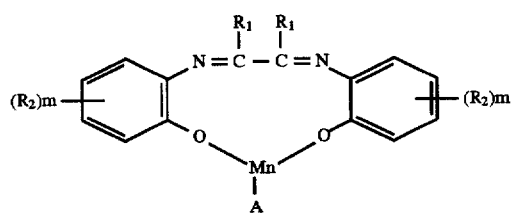 (11)
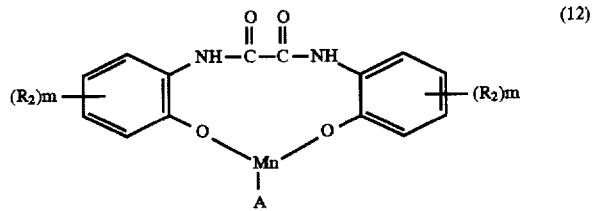 (12)

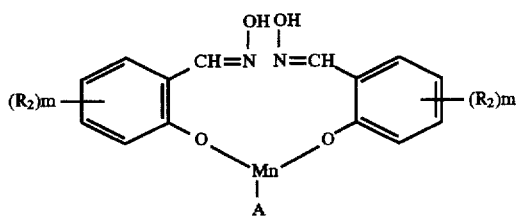

(13)

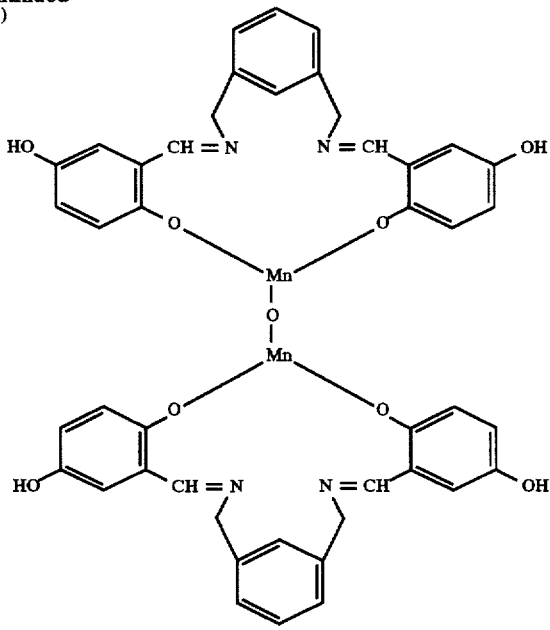

(14)

in which $R_1$ is hydrogen or optionally substituted alkyl, cycloalkyl or aryl; $R_2$ is hydrogen, optionally substituted alkyl, optionally substituted alkoxy, halogen, cyano, N(optionally substituted alkyl)$_2$, N$^{\oplus}$(optionally substituted alkyl)$_3$ or a water-solubilising group; Y is optionally substituted alkylene, cyclohexylene or arylene; $Y_1$ is $C_2$–$C_4$ alkylene, optionally interrupted by a nitrogen atom, a 1,4-methanocyclohexylene residue or a phenylene residue optionally substituted by a group $SO_3M$; M is hydrogen, an alkali metal atom, ammonium or a cation formed from an amine; n is 2 or 3; m is 0 or 1; p is 1 or 2; and A is an anion.

* * * * *